United States Patent
Huh (10) Patent No.: US 9,931,247 B2
(45) Date of Patent: Apr. 3, 2018

(54) INTERWORKING CONTROLLING METHOD OF AN ELECTRONIC EYE PROTECTION APPARATUS FOR WELDING AND A SMARTPHONE

(71) Applicant: Otos Wing. Co., Ltd., Gasan-dong, Seoul (KR)

(72) Inventor: Moon-Young Huh, Seoul (KR)

(73) Assignee: Otos Wing Co., Ltd., Seoul (KR)

( * ) Notice: Subject to any disclaimer, the term of this patent is extended or adjusted under 35 U.S.C. 154(b) by 0 days.

(21) Appl. No.: 15/205,012

(22) Filed: Jul. 8, 2016

(65) Prior Publication Data
US 2017/0007458 A1   Jan. 12, 2017

(30) Foreign Application Priority Data

Jul. 9, 2015 (KR) .................. 10-2015-0097502

(51) Int. Cl.
| | | |
|---|---|---|
| *H04M 1/00* | (2006.01) | |
| *A61F 9/06* | (2006.01) | |
| *G05B 19/406* | (2006.01) | |
| *G08C 17/02* | (2006.01) | |
| *G05B 19/042* | (2006.01) | |

(52) U.S. Cl.
CPC .......... *A61F 9/061* (2013.01); *G05B 19/0428* (2013.01); *G05B 19/406* (2013.01); *G08C 17/02* (2013.01); *G05B 2219/24015* (2013.01); *G05B 2219/25167* (2013.01); *G05B 2219/45135* (2013.01); *G05B 2219/50177* (2013.01); *G08C 2201/93* (2013.01)

(58) Field of Classification Search
None
See application file for complete search history.

(56) References Cited

U.S. PATENT DOCUMENTS

| 8,671,949 | B2 | 3/2014 | Oshima | |
|---|---|---|---|---|
| 2005/0017152 | A1 | 1/2005 | Fergason | |
| 2008/0158502 | A1* | 7/2008 | Becker | A61F 9/067 351/44 |
| 2009/0015372 | A1* | 1/2009 | Kady | G06F 1/26 340/5.54 |
| 2010/0223706 | A1 | 9/2010 | Becker | |
| 2011/0006894 | A1 | 1/2011 | Witwear | |

(Continued)

FOREIGN PATENT DOCUMENTS

| KR | 1050708 | 7/2011 |
|---|---|---|
| KR | 1103516 | 1/2012 |
| KR | 1295195 | 8/2013 |

*Primary Examiner* — Zhiyu Lu
(74) *Attorney, Agent, or Firm* — Harness, Dickey & Pierce, P.L.C.

(57) ABSTRACT

The present invention relates to the interworking controlling method of an electronic eye protection apparatus for welding and a smartphone, or more specifically, it relates to the interworking controlling method of an electronic eye protection apparatus for welding and a smartphone, which enables remote management from a smartphone by interworking history state data on utilization, operation, settings, failure of the electronic eye protection apparatus for welding, and which enables location searching and anti-theft function such as password setting of electronic eye protection apparatus for welding with a smartphone.

5 Claims, 4 Drawing Sheets

(56) References Cited

U.S. PATENT DOCUMENTS

| | | | | |
|---|---|---|---|---|
| 2011/0159918 | A1* | 6/2011 | Huh | A61F 9/067 |
| | | | | 455/556.1 |
| 2013/0291271 | A1* | 11/2013 | Becker | G06F 3/005 |
| | | | | 2/8.2 |
| 2014/0132392 | A1* | 5/2014 | Kady | G06F 21/88 |
| | | | | 340/5.54 |
| 2015/0171928 | A1* | 6/2015 | Lee | H04B 5/0031 |
| | | | | 455/41.1 |
| 2016/0045971 | A1* | 2/2016 | Holverson | B23K 9/1087 |
| | | | | 219/132 |

* cited by examiner

INTERWORKING CONTROLLING METHOD OF AN ELECTRONIC EYE PROTECTION APPARATUS FOR WELDING AND A SMARTPHONE

FIELD

The present invention relates to the interworking controlling method of an electronic eye protection apparatus for welding and a smartphone, or more specifically, it relates to the interworking controlling method of an electronic eye protection apparatus for welding and a smartphone, which enables remote management from a smartphone by interworking history state data on utilization, operation, settings, failure of the electronic eye protection apparatus for welding, and which enables location searching and anti-theft function such as password setting of electronic eye protection apparatus for welding with a smartphone.

BACKGROUND

In general, when performing a welding, cutting or grinding work, a welding mask is worn for protection of the welder's eyes from a variety of toxic substances and to block strong lights, and various kinds of convenient and secure electronic welding masks are being developed and used.

The conventional glare shielding device of electronic welding surface has been developed in order to provide the welder with a changed or fixed level of standard in terms of concentration of the shutter depending on the welding work of the environment, to allow control of shutter operation caused by welding light, and to variably control delay time of the shutter in order to prevent the light after welding from dazzling the driver which can occur in the base material after welding, so that the control switch or variable volume required for these shutter operations are mounted in various forms and provides convenience to the welder according to specifically set locations.

However, said glare shielding device according to the conventional technology, had an unpleasant problem that phone was difficult use especially in an emergency, because mobile phone ringtones were not well heard due to noise of work environment in case of an incoming call on a mobile phone during work, and the difficulty of having to take off the shield mask to pick up the phone after halting the work.

Therefore, the applicant, through KR 2009-0130323 (Dec. 24, 2009 Pending), provided a glare shielding device that has a wireless communication function, and the present inventor has come to developing the controlling method of electronic eye protection apparatus for welding, such as: setting history state of the main data such as utilization, operation, settings, failure, location, and password of a glare shielding plate (that is, automatic darkening filter (ADF)) to the main controlling method of said glare shielding device (that is, electronic eye protection apparatus for welding); remote controlling the main data of said ADF by interworking with said electronic eye protection apparatus for welding in Bluetooth communication by using the Apps by substituting said mobile phone with a smartphone; and supporting the Helps such as Instructions for Use; and preventing thefts.

Also, there was a problem of remote controlling workers who worked far away from the managing center.

SUMMARY

Technical Problem

The present invention for solving the aforementioned problems is aimed at providing a controlling method of electronic eye protection apparatus for welding, such as setting history state of the main data such as utilization, operation, settings, failure, location, and password of automatic darkening filter (ADF) on the central processing unit (CPU) of an electronic eye protection apparatus for welding; remote controlling the main data of said ADF by interworking said electronic eye protection apparatus for welding with a smartphone in Bluetooth communication by using the Apps of the smartphone; and supporting the Helps such as Instructions for Use; and preventing thefts.

Especially, it is to provide interworking an electronic eye protection apparatus for welding with a smartphone to remotely control workers who work far away from the managing center.

Technical Solution

The interworking controlling method of an electronic eye protection apparatus for welding and a smartphone, according to the present invention for solving the above-mentioned problems, is comprised of the following steps: interworking history state data on utilization, operation, settings, failure of the electronic eye protection apparatus to the smartphone; providing a mobile application that activates said data in a smartphone; and transceiving various data on the electronic eye protection apparatus for welding by interworking said smartphone and said electronic eye protection apparatus for welding with Bluetooth communication system. Herein, in the step of transceiving the various data mentioned above, once said electronic eye protection apparatus for welding is connected with said smartphone, said control command is received and executed from said smartphone in the electronic eye protection apparatus, and by remotely managing the data of an electronic eye protection apparatus for welding from the smartphone by using the mobile application of said smartphone.

In addition, according to the preferred examples of the present invention, the mobile application of said smartphone may: provide Instructions for Use and Helps of the electronic eye protection apparatus for welding; mount a GPS on said electronic eye protection apparatus for welding to enable location searching through the mobile applications of said smartphone in case of thefts and losses of said electronic eye protection apparatus for welding; generate an alarm sound to inform the user if an electronic eye protection apparatus and the smartphone departs from Bluetooth communication distance.

Advantageous Effects

When remotely controlling a worker who is using an electronic eye protection apparatus for welding according to the present invention, the communication between long distances becomes possible through the use of wide area network by interworking an eye protection apparatus with a smartphone.

Thereby it has the effect of enabling remote control of workers who are working far away from the management center.

Through an electronic eye protection apparatus for welding and the interworking technique configuration of a smartphone according to the present invention as described above, history state data on utilization, operation, settings, failure of the electronic eye protection apparatus for welding can be remotely managed from the smartphone, and an anti-theft function such as location searching and password setting of an electronic eye protection apparatus for welding can be enabled.

DETAILED DESCRIPTION

Hereinafter, the present invention will be described in detail with reference to the attached drawings.

The terms and words used in the present specification and the scope of claims are not limited to the interpretation of ordinary or dictionary meanings, and it should be interpreted as a representation in the meaning and concept which conforms to the technical idea of the present invention, according to the principle that the concept of the terms can be appropriately defined by the inventor so that he can describe his own invention in the best way. Therefore, the configuration illustrated in the examples and the drawings as described herein, is only one of the most preferred examples of the present invention, and does not represent all of the technical concept of the present invention. Therefore, at the application date of the present invention, it should be understood that there may be various equivalents and alternatives which can replace them. Here, the same reference numbers indicated in each of the drawings demonstrate like elements.

On the other hand, an electronic eye protection apparatus for welding according to the present invention mainly uses a glare shielding device which is described in KR 2009-0130323 (Application of Dec. 24, 2009) which was applied in the name of the present applicant. Therefore, the technology related to an electronic eye protection apparatus for welding that are not separately represented herein, should be understood as following the invention of the above application.

Figure 1:
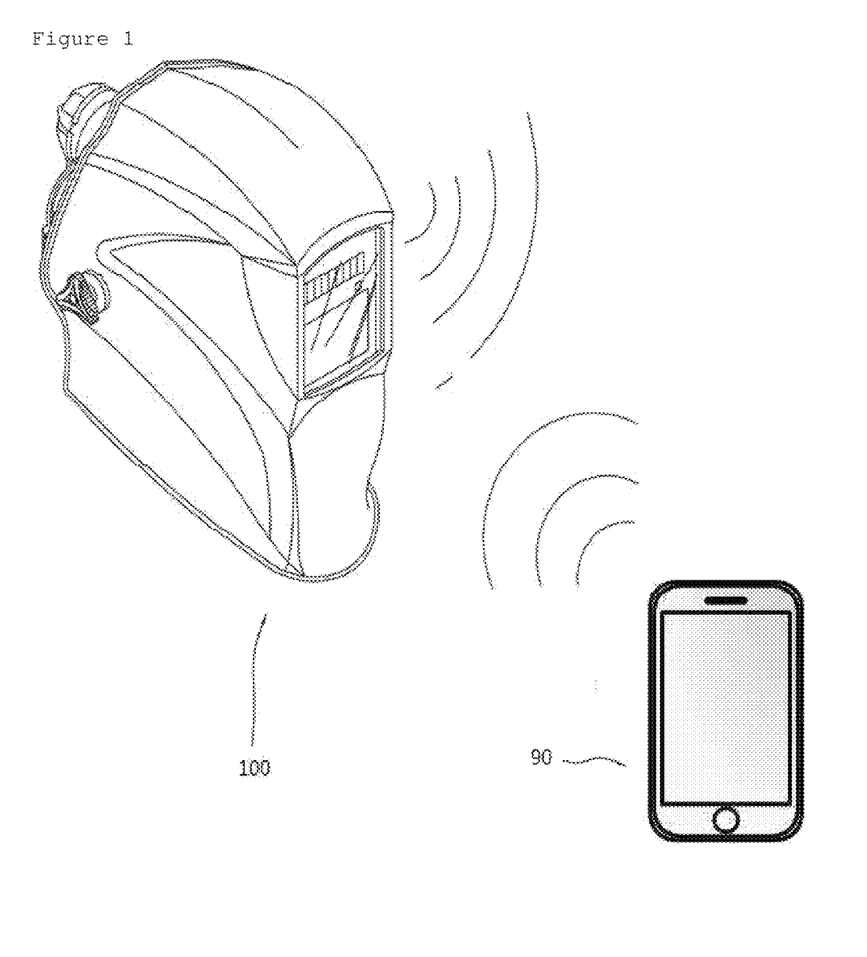
FIG. 1 is a structural drawing of the components which illustrates an example for remote controlling of an electronic eye protection apparatus for welding and a smartphone according to the present invention.
Figure 2:
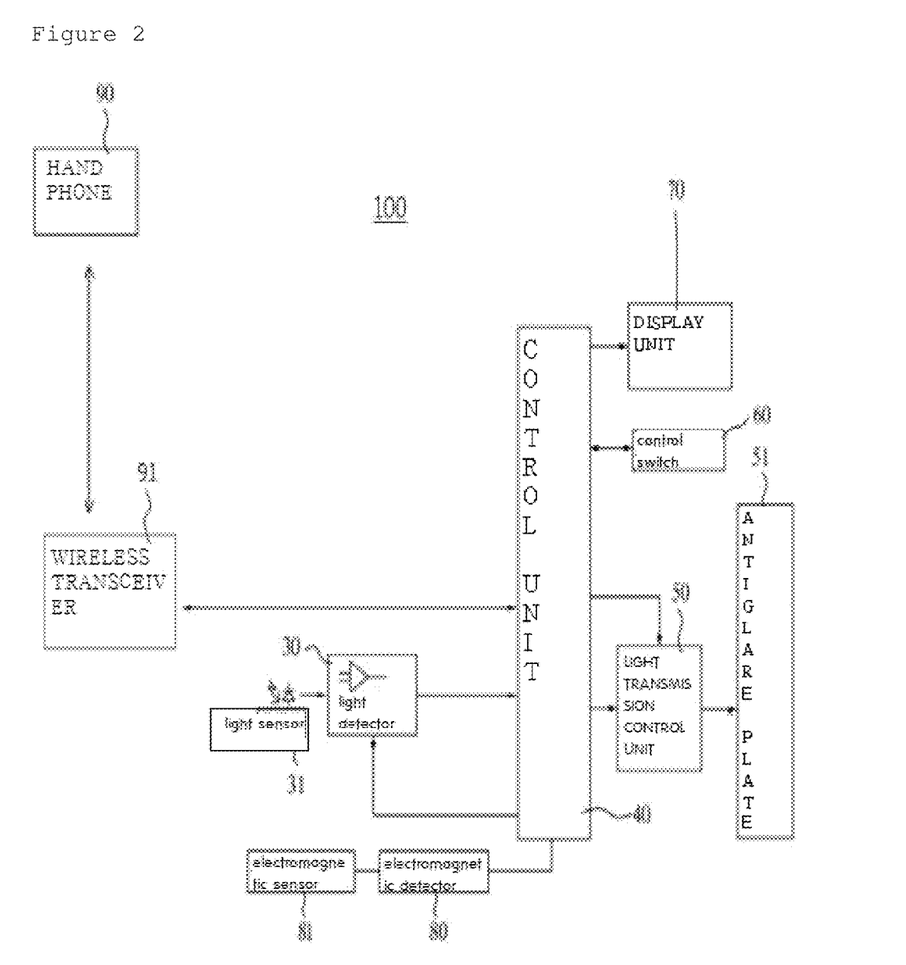
FIG. 2 is a control block drawing of an electronic eye protection apparatus for welding used in the present invention.
Figure 3:
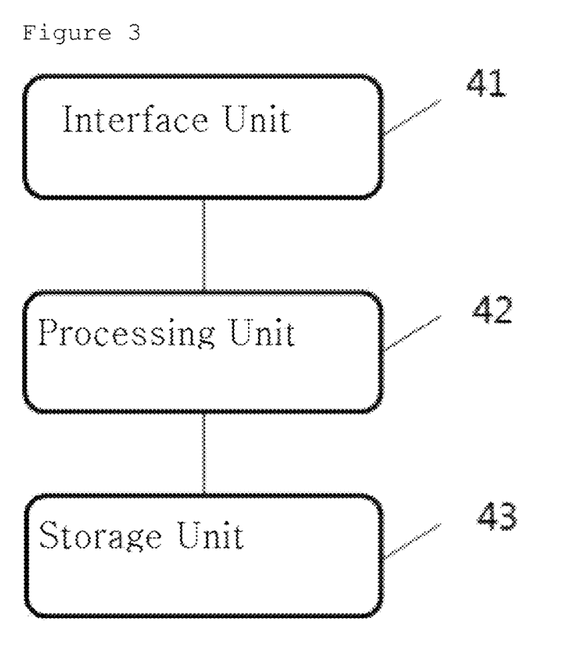
FIG. 3 is a system configuration drawing for remote controlling of an electronic eye protection apparatus for welding according to an example of the present invention.
Figure 4:
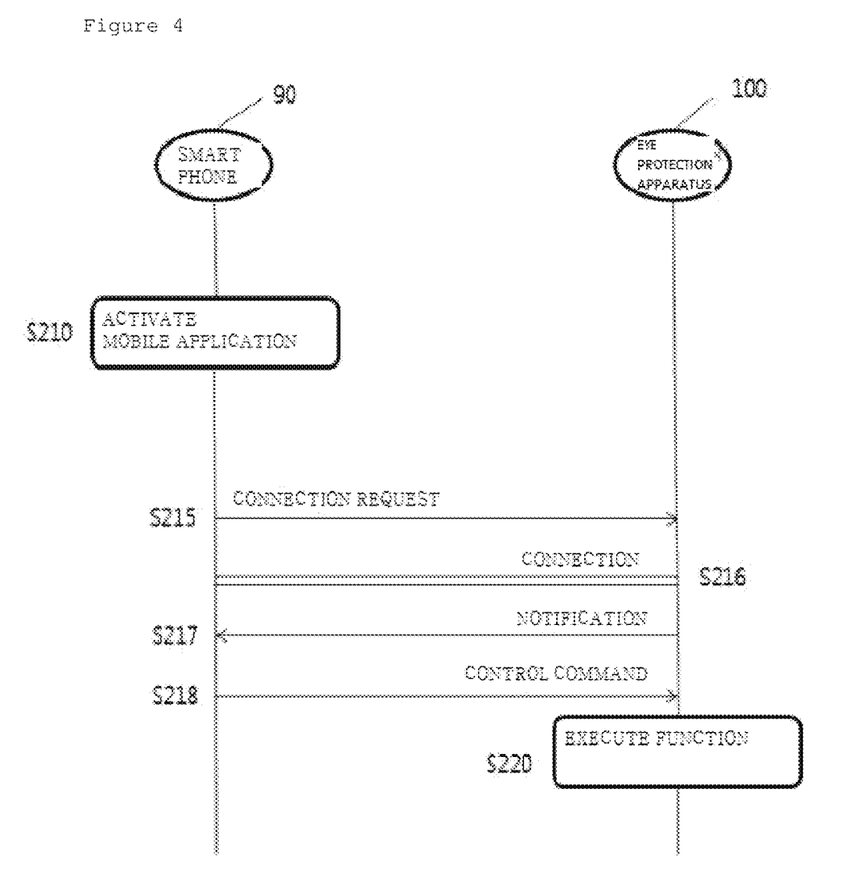
FIG. 4 is an exemplary drawing illustrating a method for remote controlling of an electronic eye protection apparatus for welding according to an example of the present invention.

FIG. 1 is a structural drawing of the components which illustrates an example for remote controlling of an electronic eye protection apparatus for welding and a smartphone according to the present invention, FIG. 2 is a control block drawing of an electronic eye protection apparatus for welding used in the present invention, FIG. 3 is a system configuration drawing for remote controlling of an electronic eye protection apparatus for welding according to an example of the present invention, and FIG. 4 is an exemplary drawing illustrating a method for remote controlling of an electronic eye protection apparatus for welding according to an example of the present invention.

As illustrated in FIG. 1, a system for remotely controlling an electronic eye protection apparatus for welding, according to the present invention, may be configured so as to include a smartphone (90) and an electronic eye protection apparatus (100).

A smartphone (90) may connect an electronic eye protection apparatus for welding to the local area wireless communication system, by activating the already stored mobile application and by using the mobile application which is activated. Here, the local area wireless communication may be a concept which covers all of Bluetooth, Zigbee, WiFi, and RFID, etc., and according to an example of the present invention, it is most appropriate to utilize Bluetooth, but should not be limited thereto.

Said smartphone (90) and the electronic eye protection apparatus for welding (100) are used independently, and said smartphone (90) is provided to the wearer of the electronic eye protection apparatus for welding to provide a remote control function by interworking with said electronic eye protection apparatus for welding. In other words, the smartphone (90) is able to remotely control the electronic eye protection apparatus for welding (100) which is connected thereto, when it is connected to the electronic eye protection apparatus for welding (100). That is, the smartphone (90) can transmit the control command which is input from the user. The interworking controlling function of the electronic eye protection apparatus for welding and the smartphone or a method thereof is to be described below.

The electronic eye protection apparatus for welding (100) may be formed in the shape of a cartridge for use in the present invention, as illustrated above in FIG. 2, and includes a light detecting means (30), a light sensor (31), a central processing unit (i.e., CPU) (40), a light transmission controlling means (50), a glare shielding plate (that is, automatic darkening filter (ADF) (51), a control switch (60), a display unit (70), an electromagnetic wave detecting means (80), an electromagnetic wave sensing means (81), and a wireless transceiver (91).

Said light detecting means (30) detects the welding light through the signal which is input from the light sensor (31), in particular, detects the light generated by the welding or a cutting torch.

Said CPU (40) sets the reference value in order to control the detection sensitivity of said light detecting means (30) based on the input of the control switch (60), and sets the light transmission density and the operational delay time of automatic darkening filter (51). Also, when the light level detected by said light detecting means (30) is more than the pre-set reference value, it is determined by the welding light, and operates the light transmission controlling means (50). In addition to this, in the present invention, the main data which is controlled by the application of the smartphone is set on said CPU (40) which will be described below, that is, the history state of the main data on operation, settings, failure, location, and password, etc. of said automatic darkening filter (51), are set.

The electronic eye protection apparatus for welding of the CPU (40) used in the present invention may be configured to include an interface unit (41), a processor unit (42), and a storage unit (43) as illustrated in FIG. 3, and hereby, an interface unit (41) may transceive various data and interwork the data to the smartphone. An interface unit (41) may be connected with the smartphone by the local area wireless communication method. In addition, the processor unit (42) may receive and transfer the control command from the smartphone (90) in the electronic eye protection apparatus for welding, if the connection is executed in the electronic eye protection apparatus for welding, depending on the choice of the user. And the processor unit (42) may convert the first control command provided from the smartphone (90) into the data of the RF communication system, that is, the second control command. Thereafter, the processor unit (42) may transmit the converted second control command, once connection is made to the electronic eye protection apparatus for welding, depending on the choice of the user.

The light transmission controlling means (50) controls the light transmissivity so that it is kept at a constant value, by operating a glare shielding plate (51) at the light transmission concentration which is set to said CPU (40).

On the other hand, an electromagnetic wave sensing means (81) detects the electromagnetic wave which is generated in said welding or a cutting torch. And an electromagnetic wave detecting means (80), which is input through said electromagnetic wave sensing means (81), is comparable to the reference value wherein the resonated signal is variably set.

Therefore, in said CPU (40), the light transmission controlling method means (50) is operated based on the user's input of the control switch (60). However to operate, the operating state is controlled by monitoring the changes of the electromagnetic wave signal from the output of said electromagnetic wave detecting method (80).

On the other hand, a wireless transceiver (91) receives a control signal of the smartphone (90) and sends it to the CPU (40). Also, wireless communication is performed by transmitting the digital signal of the CPU (40) to the smartphone (90).

At this time, it is desirable that Bluetooth communication system is applied to said wireless transceiver (91).

An electronic eye protection apparatus for welding according to the present invention may provide wireless communication between a smartphone and an electronic eye protection apparatus for welding on the basis of communication protocols used by Bluetooth 4.0.

Compared with the conventional Bluetooth 3.0, Bluetooth 4.0 has reduced power consumption, strengthened security, and can be utilized for video transmission of handphones and computers, video synchronization between a stationary device and a mobile device, and printing between a digital camera and an output device, through big data communication. It is also characterized in that power consumption becomes even lower and size is smaller, and has a low price.

As concerns said smartphone (90), it is possible to remotely control the main data of said automatic darkening filter, in other words, the history state of the main data which are set to said CPU (40), such as the utilization, operation, settings, failure, location, and password of said automatic darkening filter, by interworking with said electronic eye protection apparatus for welding and a smartphone through Bluetooth communication with the use of said smartphone of applications (Apps).

Also, it is possible to set a password through the application of said smartphone in order to prevent thefts and losses of said electronic eye protection apparatus for welding, and in case of thefts and losses, it is possible to find the location of said electronic eye protection apparatus for welding.

Here, in order to prevent thefts and losses of said electronic eye protection apparatus for welding, it is desirable to mount a GPS (not illustrated).

Hereinafter, a method of remote controlling an electronic eye protection apparatus for welding will be described, through activating the application of the smartphone according to the present invention, and connecting with an electronic eye protection apparatus for welding in the method of local area wireless communication system by using the activated mobile application.

FIG. 4 is a drawing which illustrates a method for remote controlling an electronic eye protection apparatus for welding according to an example of the present invention.

Beforehand, said automatic darkening filter used in the present invention, or more specifically, data such as the utilization, operation, settings, failure, and history state, is set to the central processing unit. Thereafter, the mobile application (S210) is activated in the smartphone (90), and with the use of the activated mobile application, connection is made with an electronic eye protection apparatus for welding through the method of local area wireless communication.

Thereafter, it can be notified (S217) to the smartphone (90) that connection is made with an electronic eye protection apparatus for welding, as a result of executing the connection with an electronic eye protection apparatus for welding which has been requested.

After that, the smartphone (90), when it is connected to an electronic eye protection apparatus for welding, receives input of a control command from the user, and the control command which is input can be transferred to an electronic eye protection apparatus for welding (S218).

From then on, an electronic eye protection apparatus for welding may execute the operation or function (S220), which a smartphone attempts to control remotely, according to the provided control command, once it is provided with a control command from the mobile application of a smartphone.

Through this method, it becomes possible to remotely control a worker who is using an electronic eye protection apparatus, since the communication between long distances becomes possible through the use of wide area network by interworking an eye protection apparatus with a smartphone. For example, a management center positioned in country A can control workers who are in different countries such as B, C and D.

The control commands received by an electronic eye protection apparatus are select button of the work, stop, change and additional work.

Of course, the mobile application of said smartphone can be provided with the Instructions for Use and the Helps of an electronic eye protection apparatus for welding, and location searching can also be enabled through the mobile application of said smartphone by mounting a GPS to said electronic eye protection apparatus for welding in case of thefts and losses of said electronic eye protection apparatus for welding. In addition, it is also possible to warn the user, if an electronic eye protection apparatus for welding and a smartphone departs from the Bluetooth communication distance.

Taken together again, according to the preferred examples of the present invention, the interworking control of an electronic eye protection apparatus for welding and a smartphone comprises the steps of: setting the utilization, operation, settings, failure, and history state of an electronic eye protection apparatus for welding; providing a mobile application that activates the data in a smartphone; and making a wireless connection to an electronic eye protection apparatus by using the mobile application of the smartphone. Various types of data of the electronic eye protection apparatus for welding is transceived by interworking the smartphone and the electronic eye protection apparatus for welding with Bluetooth communication system. The step of transceiving the various types of data is characterized in that a control command from the smartphone, which is received by the electronic eye protection apparatus for welding, is executed once the electronic eye protection apparatus for welding is connected with the smartphone, and the data of an electronic eye protection apparatus for welding is remotely managed in a smartphone by using the mobile application of the smartphone. In addition, the Instructions for Use and Helps of an electronic eye protection apparatus for welding may be provided to the mobile application of the smartphone, and location searching may be enabled through mobile applications of said smartphone in case of thefts and losses of said electronic eye protection apparatus for welding, by mounting a GPS on said electronic eye protection apparatus for welding. Also, the user may be informed with an alarm sound that an electronic eye protection apparatus has departed from Bluetooth communication distance of the smartphone.

The wireless connection between said smartphone (90) and an electronic eye protection apparatus (100) can be severed by pressing the select button of the electronic eye protection apparatus.

On the other hand, according to another example of the present invention, in case of an incoming call to the smartphone (90) using Bluetooth function, there is no need to take off the shield mask to pick up the phone.

According to another example, an electronic eye protection apparatus can be linked to the welding unit, and can receive data on welding wire speed, voltage power, electric current, temperature, gas supply speed. And the welding unit can be controlled by receiving the data sent from an electronic eye protection apparatus at the communication center.

Also, in case of an incoming call, an electronic eye protection apparatus can transfer an interrupt signal to the welding unit, and stop supplying electric current or gas. Then the welding can be aborted automatically by an incoming call. In order to begin work again, the worker can press the start work button. Such mode of automatic abort can be activated or deactivated depending on the choice of the worker. In a deactivation mode, even if there is an incoming call to the interworking smartphone (90) the worker can continue work. Such function can be operated by the function select button of an electronic eye protection apparatus, and can be operated by the application of the smartphone (90) which is interworking with an electronic eye protection apparatus (100). This allows the worker to pick up the phone safely.

The function select button of an electronic eye protection apparatus (100) can be in an appropriate size and shape so that the worker can operate it while still wearing gloves. Approximately 3 buttons can be placed separately on the outer side of an electronic eye protection apparatus. Also, said control switch (60) can become the function select button.

Also, according to one example of the present invention, the work command transferred to the worker from the management center can be transferred through a smartphone (90), and the contents of the transferred work command can be displayed on the LCD screen of an electronic eye protection apparatus (100). However, in order not to blind the sight of the worker during work, it can be displayed if the worker pushes the function button. In this case, the entire contents of the work command can be displayed directly on the whole LCD screen.

Instead, only a specific part of the LCD screen of an electronic eye protection apparatus (100) can be divided and can be displayed in the form of a simple sign or a number in relation to the work command.

The drawings and specification as described above are those describing an example of the present invention, which are merely used for the purpose of illustrating the present invention, and is not used to limit the meanings of or limit the scope of the present invention as set forth in the attached scope of claims. Therefore, it would be understood by those having ordinary knowledge in the present field of art, that various modifications and other equivalent examples are also possible. Therefore, the true scope of technical protection for the present invention should be defined by the technical spirit of the attached scope of claims.

DESCRIPTION OF THE REFERENCE NUMBERS

30: light detecting means
31: light sensor
40: central processing unit (CPU)
41: interface unit
42: processor unit
43: storage unit
50: light transmission controlling means
51: glare shielding plate
60: control switch
70: display unit
80: electromagnetic wave detecting means
81: electromagnetic wave sensing means
90: smartphone
91: wireless transceiver
100: electronic eye protection apparatus for welding

What is claimed is:

1. An interworking controlling method of an electronic eye protection apparatus for welding and a smartphone, comprising the steps of:
    setting history state data on utilization, operation, settings, and failure of the electronic eye protection apparatus;
    providing a mobile application of the smartphone that activates the history state data in a smartphone;
    wirelessly connecting the electronic eye protection apparatus and the smartphone by using the mobile application of the smartphone; and
    transceiving various data on the electronic eye protection apparatus by interworking the smartphone and the electronic eye protection apparatus with Bluetooth communication system;
    wherein the step of transceiving the various data further comprises:
        once the electronic eye protection apparatus is connected with the smartphone, receiving and executing a control command from the smartphone in the electronic eye protection apparatus, and
        remotely managing the data of an electronic eye protection apparatus from the smartphone by using the mobile application of the smartphone,
    wherein the electronic eye protection apparatus includes a function select button having an activation mode and a deactivation mode, wherein the activation mode stops supply of electric current or gas automatically aborting welding upon receipt of an incoming call to the smartphone and in the deactivation mode the incoming call to the smartphone is redirected.

2. The interworking controlling method of an electronic eye protection apparatus for welding and a smartphone according to claim 1,
    wherein the Instructions for Use and the Helps of the electronic eye protection apparatus is provided in the mobile application of the smartphone.

3. The interworking controlling method of an electronic eye protection apparatus for welding and a smartphone according to claim 1,
wherein a GPS is mounted on the electronic eye protection apparatus to enable location searching through the mobile application of the smartphone in case of thefts and losses of the electronic eye protection apparatus.

4. The interworking controlling method of an electronic eye protection apparatus for welding and a smartphone according to claim 1,
wherein an alarm sound is informed to user if the electronic eye protection apparatus and the smartphone departs from Bluetooth communication distance.

5. An interworking controlling method of an electronic eye protection apparatus for welding and a smartphone, comprising the steps of:
setting history state data on utilization, operation, settings, and failure of the electronic eye protection apparatus;
providing a mobile application of the smartphone that activates the history state data in a smartphone;
wirelessly connecting the electronic eye protection apparatus and the smartphone by using the mobile application of the smartphone;
transceiving various data on the electronic eye protection apparatus by interworking the smartphone and the electronic eye protection apparatus with Bluetooth communication system;
wherein the step of transceiving the various data further comprises:
once the electronic eye protection apparatus is connected with the smartphone, receiving and executing a control command from the smartphone in the electronic eye protection apparatus, and
remotely managing the data of an electronic eye protection apparatus from the smartphone by using the mobile application of the smartphone; and
selecting one of an activation mode and a deactivation mode, wherein the activation mode stops supply of electric current or gas automatically aborting welding upon receipt of an incoming call to the smartphone and in the deactivation mode the incoming call to the smartphone is redirected.

* * * * *